(12) United States Patent
Lee et al.

(10) Patent No.: US 11,623,065 B2
(45) Date of Patent: Apr. 11, 2023

(54) VEHICLE AND METHOD FOR CONTROLLING THE SAME

(71) Applicants: Hyundai Motor Company, Seoul (KR); Kia Motors Corporation, Seoul (KR)

(72) Inventors: Jinmo Lee, Gyeonggi-do (KR); Kaangdok Yee, Gyeonggi-do (KR); Jung Keun You, Gyeonggi-do (KR); Joongkwan Kim, Gyeonggi-do (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 808 days.

(21) Appl. No.: 16/513,304

(22) Filed: Jul. 16, 2019

(65) Prior Publication Data

US 2020/0215294 A1 Jul. 9, 2020

(30) Foreign Application Priority Data

Jan. 7, 2019 (KR) .......................... 10-2019-0001742

(51) Int. Cl.
*A61M 21/02* (2006.01)
*A61B 5/16* (2006.01)
(Continued)

(52) U.S. Cl.
CPC .......... *A61M 21/02* (2013.01); *A61B 5/1176* (2013.01); *A61B 5/165* (2013.01); *A61B 5/18* (2013.01); *B60Q 9/00* (2013.01); *B60W 10/30* (2013.01); *B60W 50/16* (2013.01); *A61B 5/0077* (2013.01); *A61B 5/02055* (2013.01); *A61M 2021/0022* (2013.01); *A61M 2021/0027* (2013.01); *A61M 2021/0044* (2013.01); *A61M 2021/0066* (2013.01); *A61M 2205/50* (2013.01); *A61M 2205/505* (2013.01); *A61M 2205/52* (2013.01); *A61M 2230/06* (2013.01); *A61M 2230/10* (2013.01); *A61M 2230/30* (2013.01);
(Continued)

(58) Field of Classification Search
None
See application file for complete search history.

(56) References Cited

U.S. PATENT DOCUMENTS

2015/0254955 A1* 9/2015 Fields ................ G06Q 30/0283
340/576
2016/0167672 A1* 6/2016 Krueger ................ G16H 40/63
340/576
2017/0352283 A1* 12/2017 Lau ........................ A61B 5/165

* cited by examiner

*Primary Examiner* — Carrie R Dorna
(74) *Attorney, Agent, or Firm* — Fox Rothschild LLP

(57) ABSTRACT

A vehicle may include: a feedback device; a bio-signal sensor configured to measure a bio-signal of a user; and a controller operatively coupled to the feedback device and the bio-signal sensor, the controller including a memory configured to store at least one program instruction and processor configured to execute the at least one program instruction. The controller may be configured to: determine information characterizing a current emotional state of the user based on the bio-signal; calculate, based on a difference value between the current emotional state and a target emotional state, an operation ratio between a first mode for controlling operation of the feedback device to decrease a degree of excitability of the user and a second mode for controlling the operation of the feedback device to increase a degree of positivity of the user; and control the operation of the feedback device for a predetermined time based on the operation ratio.

14 Claims, 9 Drawing Sheets

(51) Int. Cl.
    *A61M 21/00*    (2006.01)
    *A61B 5/18*    (2006.01)
    *A61B 5/1171*    (2016.01)
    *B60Q 9/00*    (2006.01)
    *B60W 50/16*    (2020.01)
    *B60W 10/30*    (2006.01)
    *A61B 5/00*    (2006.01)
    *A61B 5/0205*    (2006.01)
    *G06V 40/16*    (2022.01)
    *B60W 40/08*    (2012.01)

(52) U.S. Cl.
    CPC ..... *A61M 2230/50* (2013.01); *A61M 2230/65* (2013.01); *B60W 2040/0818* (2013.01); *B60W 2040/0827* (2013.01); *B60W 2040/0872* (2013.01); *B60W 2540/22* (2013.01); *B60W 2540/221* (2020.02); *G06V 40/174* (2022.01)

FIG. 7

| FEEDBACK DEVICE (150) \ MODE | SPEAKER (151) | DISPLAY (152) | VIBRATION DEVICE (153) | AIR CONDITIONER (154) |
|---|---|---|---|---|
| FIRST MODE | SOUND CORRESPONDING TO TARGET BREATHING CYCLE/ TARGET HEARTBEAT CYCLE | -IMAGE CORRESPONDING TO TARGET BREATHING CYCLE/ TARGET HEARTBEAT CYCLE<br>-IMAGE OF COLOR THAT DECREASES DEGREE OF EXCITABILITY | VIBRATION CORRESPONDING TO TARGET BREATHING CYCLE/TARGET HEARTBEAT CYCLE | -PERFUME THAT DECREASES DEGREE OF EXCITABILITY<br>-WIND THAT DECREASES DEGREE OF EXCITABILITY |
| SECOND MODE | SOUND THAT INCREASES DEGREE OF POSITIVITY | -IMAGE CORRESPONDING TO SOUND<br>-IMAGE OF COLOR THAT INCREASES DEGREE OF POSITIVITY | VIBRATION CORRESPONDING TO SOUND | -PERFUME THAT INCREASES DEGREE OF POSITIVITY<br>-WIND THAT INCREASES DEGREE OF POSITIVITY |

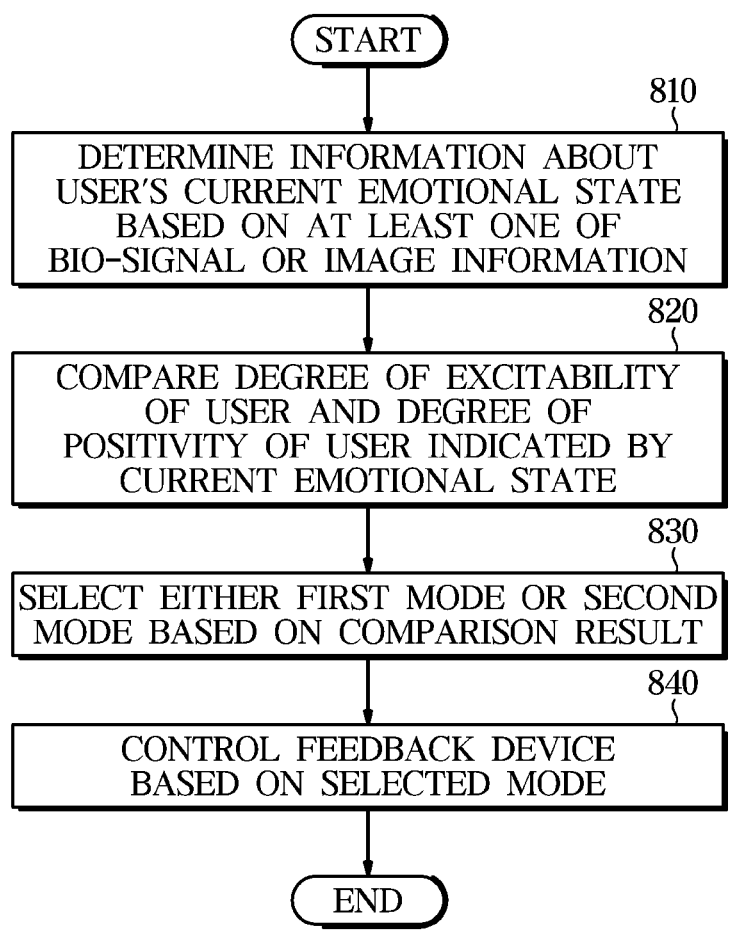

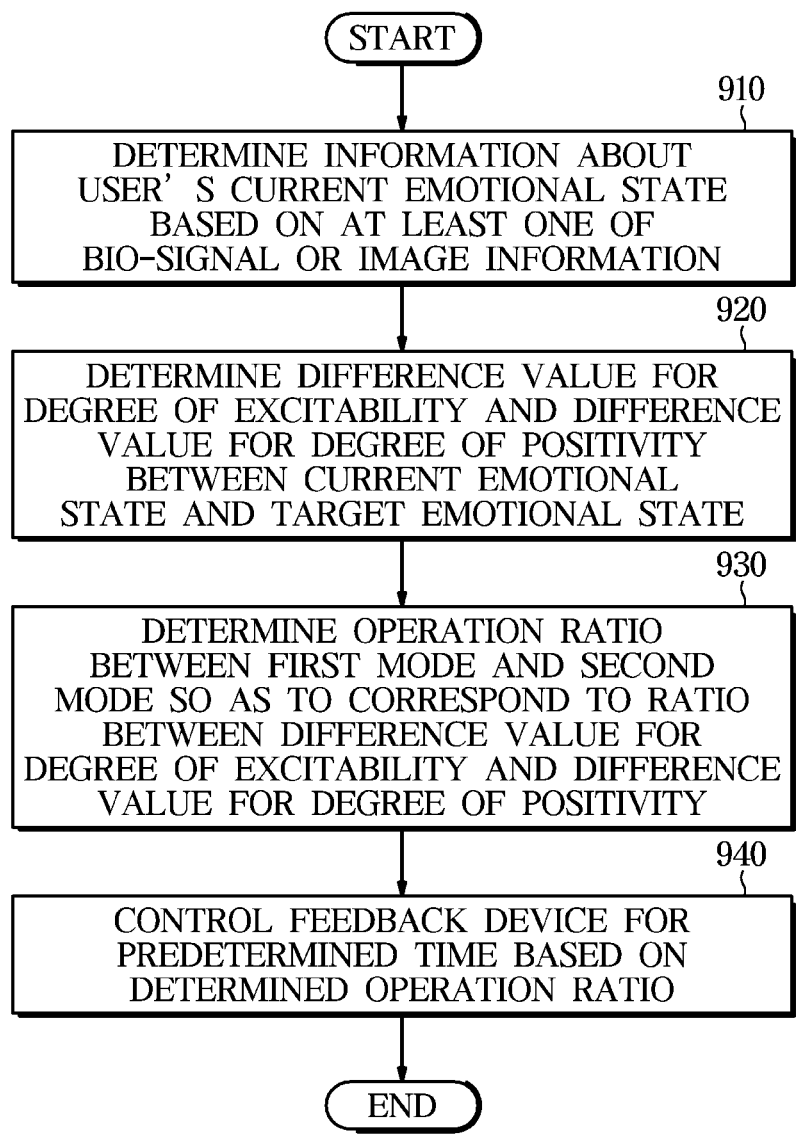

VEHICLE AND METHOD FOR
CONTROLLING THE SAME

CROSS-REFERENCE TO RELATED
APPLICATION

This application is based on and claims priority under 35 U.S.C. § 119 to Korean Patent Application No. 10-2019-0001742, filed on Jan. 7, 2019 in the Korean Intellectual Property Office, the present disclosure of which is incorporated herein by reference in its entirety.

TECHNICAL FIELD

Embodiments of the present disclosure relate to generally to vehicular technologies and, more particularly, to a vehicle with components subject to control based on a user's emotion, and a method for controlling the vehicle.

BACKGROUND

In recent years, technologies for detecting an emotional state of a vehicle user have been actively studied. Also, similar technologies for inducing a positive emotion in a vehicle user have been conducted.

However, conventional techniques are limited merely to determining the positivity or negativity of the user's emotional state. Thus, such techniques are only capable of providing feedback that regulates the output of vehicular components based on whether the determined emotional state of the user is positive or negative.

SUMMARY

Therefore, it is an aspect of the present disclosure to provide a vehicle capable of determining a mode in which a user's emotional state in the vehicle is determined as a degree of positivity and a degree of excitability. Furthermore, it is an aspect of the present disclosure to provide a vehicle capable of determining an operation ratio between a mode for controlling a feedback device that decreases the degree of excitability and a mode for controlling the feedback device that increases the degree of positivity according to the determined degree of positivity and degree of excitability. Furthermore, it is an aspect of the present disclosure to provide a method for controlling the vehicle.

Additional aspects of the present disclosure will be set forth in part in the description which follows and, in part, will be apparent from the description, or may be learned by practice of the present disclosure.

In accordance with embodiments of the present disclosure, a vehicle may include: a feedback device; a bio-signal sensor configured to measure a bio-signal of a user; and a controller operatively coupled to the feedback device and the bio-signal sensor, the controller including a memory configured to store at least one program instruction and processor configured to execute the at least one program instruction. The controller may be configured to: determine information characterizing a current emotional state of the user based on the bio-signal; calculate, based on a difference value between the current emotional state and a target emotional state, an operation ratio between a first mode for controlling operation of the feedback device to decrease a degree of excitability of the user and a second mode for controlling the operation of the feedback device to increase a degree of positivity of the user; and control the operation of the feedback device for a predetermined time based on the operation ratio.

The controller may control the feedback device, based on the operation ratio, such that the feedback device performs the first mode for a first time of the predetermined time and performs the second mode for a second time of the predetermined time, wherein the second time equals a difference between the predetermined time and the first time.

The controller may control the feedback device such that the first mode and the second mode are repeatedly alternately performed based on a predetermined number of mode switching times and a predetermined holding time for each mode.

The controller may perform an operation through a neural network based on the current emotional state and the target emotional state; determine the number of mode switching times and the holding time for each mode corresponding to the current emotional state and the target emotional state based on information characterizing the operation performed through the neural network; and control the operation of the feedback device such that the first mode and the second mode are repeatedly alternately performed based on the determined number of mode switching times and the determined holding time for each mode.

The controller may determine the degree of excitability of the user and the degree of positivity of the user based on the current emotional state, to compare the degree of excitability of the user with the degree of positivity of the user, and to perform either the first mode or the second mode based on the comparison of the degree of excitability of the user with the degree of positivity of the user.

The controller may calculate a first difference value between the degree of excitability for the current emotional state and the degree of excitability for the target emotional state calculate, to calculate a second difference value between the degree of positivity for the current emotional state and the degree of positivity for the target emotional state calculate, and to calculate the operation ratio between the first mode and the second mode as equivalent to a ratio between the first difference value and the second difference value.

The feedback device may be disposed in the vehicle and include at least one of a speaker, a display, an air conditioner, and a vibration device installed in a seat.

The controller may extract an emotion factor that affects the current emotional state; in the first mode, control the operation of the feedback device causing an emotion factor to decrease according to the degree of excitability of the extracted emotion factor; and in the second mode, control the operation of the feedback device causing an emotion factor to increase according to the degree of positivity of the extracted emotion factor.

Furthermore, in accordance with embodiments of the present disclosure, a method for controlling a vehicle, the vehicle including a feedback device, a bio-signal sensor configured to measure a bio-signal of a user, and a controller operatively coupled to the feedback device and the bio-signal sensor, may include: determining, by the controller, information characterizing a current emotional state of the user based on the bio-signal; calculating, by the controller, based on a difference value between the current emotional state and a target emotional state, an operation ratio between a first mode for controlling the operation of the feedback device to decrease a degree of excitability of the user and a second mode for controlling the operation of the feedback device to increase a degree of positivity of the user; and controlling, by the controller, the operation of the feedback device for a predetermined time based on the operation ratio.

The controlling of the feedback device may include controlling the operation of the feedback device, based on the operation ratio, such that the feedback device performs the first mode for a first time of the predetermined time and performs the second mode for a second time of the predetermined time, wherein the second time equals a difference between the predetermined time and the first time.

The controlling of the feedback device may include controlling the operation of the feedback device such that the first mode and the second mode are repeatedly alternately performed based on a predetermined number of mode switching times and a predetermined holding time for each mode.

The controlling of the feedback device may include performing an operation through a neural network based on the current emotional state and the target emotional state; determining the number of mode switching times and the holding time for each mode corresponding to the current emotional state and the target emotional state based on information characterizing the operation performed through the neural network; and controlling the operation of the feedback device such that the first mode and the second mode are repeatedly alternately performed based on the determined number of mode switching times and the determined holding time for each mode.

The controlling of the feedback device may include determine the degree of excitability of the user and the degree of positivity of the user based on the current emotional state; comparing the degree of excitability of the user with the degree of positivity of the user; and performing either the first mode or the second mode based on the comparison of the degree of excitability of the user with the degree of positivity of the user.

The calculating of the operation ratio may include calculating a first difference value between the degree of excitability for the current emotional state and the degree of excitability for the target emotional state calculate; calculating a second difference value between the degree of positivity for the current emotional state and the degree of positivity for the target emotional state calculate; and calculating the operation ratio between the first mode and the second mode as equivalent to a ratio between the first difference value and the second difference value.

The feedback device may be disposed in the vehicle and include at least one of a speaker, a display, an air conditioner, and a vibration device installed in a seat.

The controlling of the feedback device may include extracting an emotion factor that affects the current emotional state; in the first mode, controlling the operation of the feedback device causing an emotion factor to decrease according to the degree of excitability of the extracted emotion factor; and in the second mode, controlling the operation of the feedback device causing an emotion factor to increase according to the degree of positivity of the extracted emotion factor.

BRIEF DESCRIPTION OF THE DRAWINGS

These and/or other aspects of the present disclosure will become apparent and more readily appreciated from the following description of the embodiments, taken in conjunction with the accompanying drawings of which:

FIG. 7 is a view illustrating control of the feedback device according to each mode in the vehicle according to embodiments of the present disclosure;

FIG. 8 is a flowchart illustrating a method of controlling the feedback device in a method of controlling the vehicle according to embodiments of the present disclosure; and FIG. 9 is another flowchart illustrating a method of controlling the feedback device in a method of controlling the vehicle according to embodiments of the present disclosure.

Figure 1:
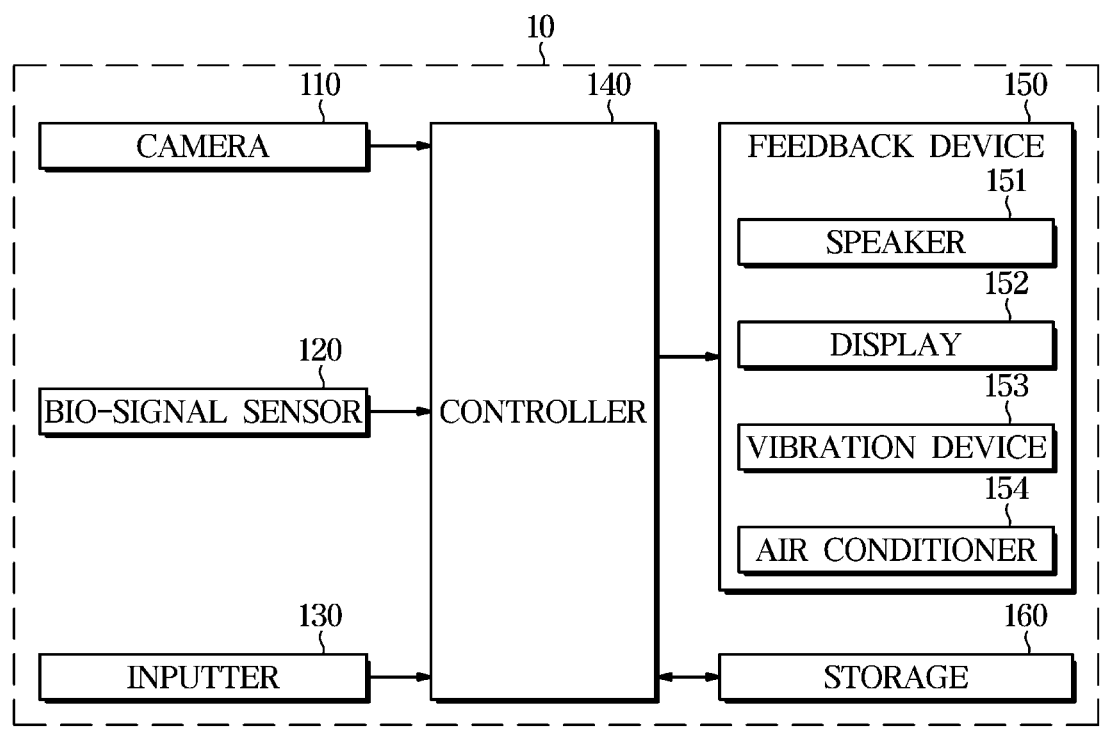
FIG. 1 is a control block diagram of a vehicle according to embodiments of the present disclosure.

It should be understood that the above-referenced drawings are not necessarily to scale, presenting a somewhat simplified representation of various preferred features illustrative of the basic principles of the present disclosure. The specific design features of the present disclosure, including, for example, specific dimensions, orientations, locations, and shapes, will be determined in part by the particular intended application and use environment.

DETAILED DESCRIPTION OF THE EMBODIMENTS

Hereinafter, embodiments of the present disclosure will be described in detail with reference to the accompanying drawings. As those skilled in the art would realize, the described embodiments may be modified in various different ways, all without departing from the spirit or scope of the present disclosure. Like numbers refer to like elements throughout this specification. This specification does not describe all components of the embodiments, and general information in the technical field to which the present disclosure belongs or overlapping information between the embodiments will not be described.

It will be understood that when a component is referred to as being "connected" to another component, it can be directly or indirectly connected to the other component. When a component is indirectly connected to another component, it may be connected to the other component through a wireless communication network.

Also, it will be understood that the terms "includes," "comprises," "including," and/or "comprising," when used in this specification, specify the presence of a stated component, but do not preclude the presence or addition of one or more other components.

Also, it is to be understood that the singular forms "a," "an," and "the" include plural referents unless the context clearly dictates otherwise.

As used herein, the terms "portion," "unit," "block," "member," or "module" refer to a unit that can perform at least one function or operation. For example, these terms may refer to at least one process which is performed by at least one piece of hardware such as a field-programmable gate array (FPGA) and an application specific integrated circuit (ASIC), and at least one piece of software stored in a memory, or a processor.

Reference numerals used in operations are provided for convenience of description, without describing the order of the operations, and the operations can be executed in a different order from the stated order unless a specific order is definitely specified in the context.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g., fuels derived from resources other than petroleum). As referred to herein, a hybrid vehicle is a vehicle that has two or more sources of power, for example both gasoline-powered and electric-powered vehicles.

Additionally, it is understood that one or more of the below methods, or aspects thereof, may be executed by at least one controller. The term "controller" may refer to a hardware device that includes a memory and a processor. The memory is configured to store program instructions, and the processor is specifically programmed to execute the program instructions to perform one or more processes which are described further below. The controller may control operation of units, modules, parts, devices, or the like, as described herein. Moreover, it is understood that the below methods may be executed by an apparatus comprising the controller in conjunction with one or more other components, as would be appreciated by a person of ordinary skill in the art.

Furthermore, the controller of the present disclosure may be embodied as non-transitory computer readable media containing executable program instructions executed by a processor. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed throughout a computer network so that the program instructions are stored and executed in a distributed fashion, e.g., by a telematics server or a Controller Area Network (CAN).

Hereinafter, embodiments of the present disclosure will be described in detail with reference to the accompanying drawings.

FIG. 1 is a control block diagram of a vehicle according to embodiments of the present disclosure.

As shown in FIG. 1, a vehicle 10 according to embodiments of the present disclosure may include a camera 110 for capturing a user entering the vehicle 10 and obtaining image data of the user, a bio-signal sensor 120 for measuring a bio-signal of the user, an inputter 130 for receiving an input from the user, a controller 140 for determining the user's current emotional state based on at least one of the image data of the user or the bio-signal and determining an operation ratio between a first mode for controlling a feedback device 150 so as to decrease a degree of excitability of the user and a second mode for controlling the feedback device 150 so as to increase the degree of positivity of the user based on a difference value between the determined current emotional state and a target emotional state, the feedback device 150 provided in the vehicle 10 for outputting feedback that causes the user's emotion to be a target emotion under the control of the controller 140, and a storage 160 for storing various information required for controls of the vehicle 10.

The camera 110 may capture the user in the vehicle 10 to obtain the image data of the user. The image data of the user may include information characterizing the user's facial expression, i.e., a motion of the facial body composition.

The camera 110 may include a plurality of lenses and an image sensor. The image sensor may include a plurality of photodiodes for converting light into electrical signals, and the plurality of photodiodes may be arranged in a two-dimensional matrix.

In addition, the camera 110 may be an infrared camera for capturing the user during night driving. Also in this case, the image data of the user may include information characterizing the user's facial expression.

The camera 110 may be installed on a dashboard, a windshield or a seat of the vehicle 10. However, there is no limitation on the installation position and number of the cameras 110. The image data of the user, obtained by the camera 110, may be used by the controller 140 to identify the user's facial expression and the user's position. Therefore, the camera 110 may be installed in front of the user.

At this time, the user may include both a driver and a passenger of the vehicle 10. The camera 110 may obtain the image data of each of the users in the vehicle 10.

The bio-signal sensor 120 according to embodiments of the present disclosure may measure a bio-signal of each of the users in the vehicle 10. The bio-signal of the user may be transmitted to the controller 140 and stored in the storage 160.

The bio-signal sensor 120 may be installed at various positions in the vehicle 10. For example, the bio-signal sensor 120 may be provided on the seat, a seat belt, a steering wheel, and a handle provided on a door.

In addition, the bio-signal sensor 120 may be provided as a kind of wearable device that the user who entered the vehicle 10 can wear.

The bio-signal sensor 120 may include at least one of a galvanic skin response (GSR) sensor for measuring skin electrical conductivity depending on a sweat rate of the user, a skin temperature sensor for measuring a skin temperature of the user, a heart rate (HR) sensor for measuring a heart rate of the user, an electroencephalogram (EEG) sensor for measuring brainwaves of the user, a voice recognition sensor for measuring a voice signal of the user, a blood pressure measurement sensor for measuring a blood pressure of the user, or an eye tracker for tracking the positions of pupils. However, sensors that may be included in the bio-signal sensor 120 are not limited to the above-mentioned sensors, and the bio-signal sensor 120 may include another sensor capable of measuring a person's bio-signal.

The inputter 130 according to embodiments of the present disclosure may receive an input from the user. Particularly, the inputter 130 may receive an input for the target emotional state, an input for a drive mode (e.g., the first mode and the second mode) of the feedback device 150, and an input for a mode switching pattern (e.g., number of mode switching times, mode holding times), etc. from the user.

For this, the inputter 130 may be provided in a center fascia (not shown) installed at the center of a dashboard and may be implemented with mechanical buttons, knobs, touch pad, touch screen, stick-type manipulation device, trackball, or the like. At this time, the inputter 130 disposed on the touch screen may be provided on a display 152 provided inside the vehicle 10. However, the position and implementation method of the inputter 130 are not limited to the above-described example, and may be included without limitation as long as the position and the implementation method in which the user's input can be received.

The controller 140 according to embodiments of the present disclosure may determine the user's current emotional state based on at least one of the image data of the user or the bio-signal, and control the feedback device 150 based on the determined current emotional state.

Particularly, the controller 140 may determine a facial expression of the user based on the image data of the user, and obtain information characterizing an emotional state corresponding to the facial expression. A configuration for obtaining information characterizing the user's emotional state based on image data will be described in detail later.

In addition, the controller 140 may obtain information characterizing the user's emotional state corresponding to the bio-signal of the user based on the bio-signal of a passenger 200. A configuration for obtaining information characterizing the user's emotional state based on the bio-signal will be described in detail later.

The controller 140 may determine the user's current emotional state based on at least one of the image data of the user or the bio-signal, and control the feedback device 150 based on the determined user's current emotional state.

Particularly, the controller 140 may compare the degree of excitability of the user and the degree of positivity of the user indicated by the current emotional state, and select either the first mode for controlling the feedback device 150 in a direction of decreasing the degree of excitability of the user or the second mode for controlling the feedback device 150 in a direction of increasing the degree of positivity of the user based on the comparison result. That is, the controller 140 may determine the operation ratio between the first mode and the second mode to 100 to 0 or 0 to 100 for immediate feedback on the current emotional state according to the embodiment. Accordingly, the controller 140 may control the feedback device 150 to operate in either the first mode or the second mode.

That is, the controller 140 may determine the user's current emotional state by quantifying the degree of excitability and degree of positivity. A detailed explanation will be described later.

In this case, when a numerical value of the degree of excitability indicated by the current emotional state is higher than the numerical value of the degree of negativity indicated by the current emotional state, the controller 140 may control the feedback device 150 to operate in the first mode. When the numerical value of the degree of excitability indicated by the current emotional state is lower than the numerical value of the degree of negativity indicated by the current emotional state, the controller 140 may control the feedback device 150 to operate in the second mode.

At this time, the numerical value of the degree of negativity may correspond to the numerical value of the degree of positivity having a minus (−) value. In the comparison between the numerical value of the degree of excitability and the numerical value of the degree of negativity, it is premised that the comparison is made based on an absolute value of each numerical value.

In addition, the controller 140 may determine the operation ratio between the first mode and the second mode based on the difference value between the user's current emotional state and the target emotional state, and control the feedback device 150 based on the determined operation ratio for a predetermined time.

The controller 140 may determine the difference value between the user's current emotional state and the target emotional state based on at least one of the image data of the user and the bio-signal. The target emotional state may be set when the vehicle 10 is designed, or may be set based on the user's input through the inputter 130.

The difference value between the user's current emotional state and the target emotional state may include a difference value for the degree of excitability and a difference value for the degree of positivity. That is, the controller 140 may compare the degree of excitability and the degree of positivity of the target emotional state on the basis of the determined degree of excitability and the determined degree of positivity, respectively, and determine the difference value for the degree of excitability and the difference value for the degree of positivity.

At this time, the controller 140 may determine the operation ratio between the first mode and the second mode so as to correspond to the ratio between the difference value for the degree of excitability and the difference value for the degree of positivity between the current emotional state and the target emotional state.

Thereafter, the controller 140 may control the feedback device 150 to perform the first mode for a first time of the predetermined time. The controller 140 may control the feedback device 150 to perform the second mode for a second time of the predetermined time, the second time equaling a difference between the predetermined time and the first time.

The predetermined time may be set when the vehicle 10 is designed, or may be set based on the user's input through the inputter 130. In addition, the predetermined time may correspond to an estimated driving time to a destination calculated by the controller 140 according to the user's destination input through the inputter 130.

The controller 140 may control the feedback device 150 such that the first mode and the second mode are alternately performed, repeatedly, based on a predetermined number of mode switching times and a predetermined holding time for each mode.

The predetermined number of mode switching times and the predetermined holding time for each mode may be set when the vehicle 10 is designed, or may be set based on the user's input through the inputter 130.

That is, the controller 140 may control the feedback device 150 such that the first mode and the second mode are repeatedly alternately performed. At this time, the total time that the feedback device 150 operates in the first mode may correspond to the first time of the predetermined time, and the total time that the feedback device 150 operates in the second mode may correspond to a second time of the predetermined time, the second time equaling a difference between the predetermined time and the first time.

In addition, the controller 140 may perform an operation through a neural network on the current emotional state and the target emotional state, determine the number of mode switching times and the holding time for each mode corresponding to the current emotional state and the target emotional state based on information characterizing the operation performed through the neural network, and control the feedback device 150 such that the first mode and the second mode are repeatedly alternately performed based on the determined number of mode switching times and the determined holding time for each mode.

Particularly, the controller 140 may perform the operation through the neural network on the determined current emotional state and the target emotional state, determine the number of mode switching times, and determine an operation pattern of the feedback device 150 based on the information characterizing the operation performed through the neural network.

At this time, the operation pattern of the feedback device 150 may correspond to the mode in which the feedback device 150 operates by switching the mode for the predetermined time based on the number of times an operation mode is switched for the predetermined time and the holding time for each mode.

In this case, the information characterizing the operation performed through the neural network may include information characterizing the number of mode switching times indicating the number of times the mode is switched during the predetermined time and information characterizing the holding time for each mode indicating a time at which the mode for each mode to be switched is held.

The above-mentioned neural network refers to machine learning that forms a neural structure capable of performing deep learning, so that a weight and bias corresponding to the configuration of the neural network continuously changes, thereby improving the reliability of learning.

Particularly, the vehicle 10 may improve the inference result of the neural network by continuously updating the weight, bias and activation function included in the neural network based on the current emotional state, the target emotional state, and information characterizing an arrival time of the user's emotion according to the pattern of the feedback device 150 to the target emotion. That is, the vehicle 10 may store the determined pattern and the information characterizing the arrival time of the user's emotion to the target emotion whenever the vehicle 10 drives, and continuously update the stored neural network based on information characterizing the stored determined pattern and the information characterizing the arrival time.

At this time, the neural network may be stored in the storage 160 in the form of a computer program. Hereinafter, the operation performed by the neural network in the coding form of the computer program will be described. However, the present disclosure is not limited to the computer program in which the neural network is stored.

Meanwhile, the neural network may include a Convolution Neural Network (CNN) that generates a feature map output by convoluting the current emotional state and the target emotional state, and inputs the feature map to the neural network. However, the neural network may be performed with other deep-running algorithms including Recurrent Neural Networks (RNN).

In this way, the vehicle 10 may determine the operation pattern of the feedback device 150 that is most suitable based on the current emotional state and the target emotional state through the neural network that is continuously updated according to the use. That is, the controller 140 may determine the number of mode switching times and the holding time for each mode in which the user's emotion can quickly reach the target emotion, based on the current emotional state and the target emotional state.

However, the controller 140 may control the feedback device 150 to operate in either the first mode or the second mode based on the user's input through the inputter 130.

The controller 140 may control the feedback device 150 based on the emotion of any one of the users selected through the inputter 130 from the plurality of users who entered the vehicle 10.

In addition, the controller 140 may control the feedback device 150 based on the user's emotion corresponding to the current emotional state having the highest difference value from the target emotional state, based on the current emotional state of each of the plurality of users in the vehicle 10.

Hereinafter, the control of the feedback device 150 of the controller 140 according to the modes will be described in detail.

The controller 140 may extract an emotion factor that affects the user's current emotional state and control the feedback device 150 in a direction of decreasing the emotion factor corresponding to the degree of excitability of the extracted emotion factor in the first mode, and control the feedback device 150 in a direction of increasing the emotion factor corresponding to the degree of positivity of the extracted emotion factors in the second mode.

The feedback device 150 may include at least one of a speaker 151, the display 152, an air conditioner 154 provided in the vehicle 10, and a vibration device 153 provided in the seat of the vehicle 10.

The speaker 151 may output sound to the inside of the vehicle 10 having a frequency corresponding to a target breathing cycle or a target heartbeat cycle in the first mode under the control of the controller 140, or output sound to the inside of the vehicle 10 that increases the emotion factor corresponding to the degree of positivity in the second mode under the control of the controller 140.

That is, the controller 140 may set a breathing cycle and a heartbeat cycle when the target emotional state is the target breathing cycle and the target heartbeat cycle, respectively, and control the speaker 151 to output sound corresponding to the target breathing cycle or the target heartbeat cycle to the inside of the vehicle 10 so that the degree of excitability of the user is decreased in the first mode. Accordingly, the vehicle 10 can cause the user's breathing cycle to be induced to the target breathing cycle or the user's heartbeat cycle to be induced to the target heartbeat cycle.

At this time, the sound that increases the emotion factor corresponding to the degree of positivity may be set when the vehicle 10 is designed, and may correspond to sound that has at least one of a size, a genre, an equalizer, a tone color, and a sound wave region of the sound in which the user can feel a positive emotion. For example, the sound that increases the emotion factor corresponding to the degree of positivity may include hip-hop music, classical music, and pop music in which the user can feel the positive emotion. However, the sound that increases the emotion factor corresponding to the degree of positivity may be set based on the user's input through the inputter 130. That is, the user may set the sound that caused the positive emotion to be the sound that increases the emotion factor corresponding to the degree of positivity, and the sound that is set can be stored in the storage 160.

For this, the speaker 151 may be provided inside the vehicle 10, and may be provided without limitation as long as it is in a position where the user can listen to the sound outputted.

The display 152 according to embodiments of the present disclosure may output an image having a frequency corresponding to the target breathing cycle or the target heartbeat cycle to the inside of the vehicle 10 in the first mode, and output the image having the frequency corresponding to the sound for increasing the emotion factor corresponding to the degree of positivity to the inside of the vehicle 10 in the second mode, under the control of the controller 140.

More particularly, the controller 140 may control the display 152 to increase or decrease the intensity of light output according to the frequency corresponding to the target breathing cycle or the target heartbeat cycle in the first mode, and control the display 152 to increase or decrease the intensity of the light output according to the frequency corresponding to the sound that increases the emotion factor corresponding to the degree of positivity in the second mode.

The display 152 may also output an image of a color that decreases the emotion factor corresponding to the degree of excitability in the first mode based on the control of the controller 140, and output the image of the color that increases the emotion factor corresponding to the positivity of the image in the second mode, under the control of the controller 140.

At this time, the color for decreasing the emotion factor corresponding to the degree of excitability and the color for increasing the emotion factor corresponding to the degree of positivity may be set when the vehicle 10 is designed, may be set by the controller 140 based on correlation information between the color and the emotion factor obtained from an external server, and may be set by the user through the inputter 130.

For this, the display 152 may be provided within the vehicle 10 and may include a panel. For example, the display 152 may be provided in a cluster, provided across the cluster and the center fascia, and provided in a ceiling or the door inside the vehicle 10.

The panel may be at least one of a cathode ray tube (CRT) panel, a liquid crystal display (LCD) panel, a light emitting diode (LED) panel, an organic light emitting diode (OLED) panel, a plasma display panel (PDP), and a field emission display (FED) panel.

The position and number of the displays 152 may be included without limitation as long as the position and number of the pieces of information can be visually transmitted to the user of the vehicle 10.

The vibration device 153 according to embodiments of the present disclosure may output a vibration having a frequency corresponding to the target breathing cycle or the target heartbeat cycle in the first mode, or output the vibration having the frequency corresponding to the sound for increasing the emotion factor corresponding to the degree of positivity in the second mode, under the control of the controller 140.

At this time, the outputted vibration causes the seat provided in the vehicle 10 to vibrate, and may be transmitted to the user located on the seat through the seat.

For this, the vibration device 153 may be provided in the seat provided in the vehicle 10, and may correspond to a motor driven under the control of the controller 140.

At this time, the vibration device 153 may rotate to correspond to the frequency transmitted from the controller 140 and transmit the vibration corresponding to the frequency to the user on the seat.

Further, according to the embodiment, the vibration device 153 may also include a diaphragm for amplifying the vibration.

The air conditioner 154 may output at least one of a perfume and wind that decreases the emotion factor corresponding to the degree of excitability in the first mode, and output at least one of the perfume and wind that increases the emotion factor corresponding to the degree of positivity in the second mode, under the control of the controller 140.

At this time, the perfume and wind that decrease the emotion factor corresponding to the degree of excitability may be set when the vehicle 10 is designed, may be set by the controller 140 based on the correlation information between the perfume and the emotion factor obtained from the external server, and may be set by the user through the inputter 130. For example, the perfume and wind that decrease the emotion factor corresponding to the degree of excitability may correspond to jasmine perfume and a breeze, respectively. However, the present disclosure is not limited thereto, and any perfume that can decrease the emotion factor corresponding to the degree of excitability may be included without limitation. Also, the wind that decreases the emotion factor corresponding to the degree of excitability may correspond to wind having at least one of wind direction, intensity, and temperature that can lower the degree of excitability.

In addition, the perfume and wind that decrease the emotion factor corresponding to the degree of positivity may be set when the vehicle 10 is designed, may be set by the controller 140 based on the correlation information between the perfume and the emotion factor obtained from the external server, and may be set by the user through the inputter 130. For example, the perfume and wind that increase the emotion factor corresponding to the degree of positivity may correspond to lemon perfume and a cool breeze, respectively. However, the present disclosure is not limited thereto, and any perfume that can increase the emotion factor corresponding to the degree of positivity may be included without limitation. Also, the wind that increases the emotion factor corresponding to the degree of positivity may correspond to wind having at least one of wind direction, intensity, and temperature that can raise the degree of positivity.

For this, the air conditioner 154 may be provided in the vehicle 10 to blow wind (warm air or cool air) to the indoor space of the vehicle 10 under the control of the controller 140.

More particularly, the air conditioner 154 may include a compressor, a condenser, an expansion valve, and a heat exchanger, and the compressor, the condenser, the expansion valve, and the heat exchanger may be connected to each other through at least one refrigerant passage. A refrigerant may flow through the compressor, the condenser, the expansion valve, and the heat exchanger along the refrigerant passage, and the air conditioner 154 may obtain cold air or warm air depending on a change in the state of the flowing refrigerant. The cold air or warm air may be provided to the indoor space of the vehicle 10 through a fan.

The air conditioner 154 may include a motor for driving the fan that generates wind blowing into the indoor space of the vehicle 10, and also include a motor for adjusting a wing member (not shown) provided in air vents 141 to adjust a direction of the blowing wind.

In addition, the air conditioner 154 may include an aroma actuator that injects aroma substances in wind blowing into the indoor space, and the aroma actuator may include a plurality of storage tanks for storing various kinds of aroma substances, an injection port for injecting aroma substances, and a motor for injecting aroma substances through the injection port.

In this way, the controller 140 may control at least one of the speaker 151, the display 152, the vibration device 153, and the air conditioner 154 corresponding to the feedback device 150 to induce the user's positive emotion and decrease the degree of excitability of the user.

The controller 140 may include at least one memory storing a program for performing the above-described operations and operations which will be described below, and at least one processor for executing the stored program. When there are a plurality of memories and processors, they may be integrated into one chip or provided at physically separated positions.

The storage 160 according to embodiments of the present disclosure may store various information required for controls of the vehicle 10.

For example, the storage 160 may store the image data obtained by the camera 110, a measured value obtained by the bio-signal sensor 120, correlation information between the user's bio-signal and an emotion factor, correlation information between the user's facial expression and an emotion factor, the user's emotion information, an emotion model, and the like. Data stored in the storage 160 may be transmitted to the controller 140.

The storage 160 may be implemented as at least one of a non-volatile memory device (for example, a cache, Read Only Memory (ROM), Programmable ROM (PROM), Erasable Programmable ROM (EPROM), Electrically Erasable Programmable ROM (EEPROM), and flash memory), a volatile memory device (for example, Random Access Memory (RAM)), or storage medium, such as Hard Disk Drive (HDD) and Compact Disc Read Only Memory (CD-ROM), although not limited to these. The storage 160 may be a memory implemented as a separate chip, or the storage 160 and the processor may be integrated into a single chip.

Hereinafter, the vehicle 10 for obtaining information characterizing the user's emotional state based on the image data obtained by the vehicle 10 through the camera 110 and the bio-signal obtained through the bio-signal sensor 120 will be described in detail.

Figure 2:
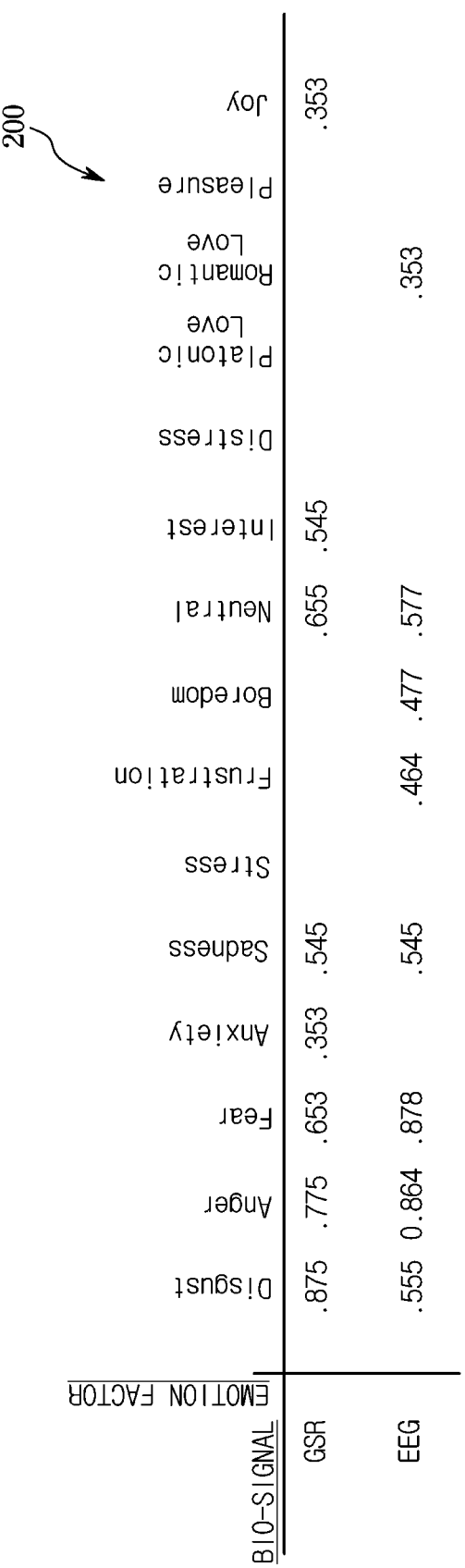
FIG. 2 is a view illustrating correlation information between bio-signals and emotion factors according to embodiments of the present disclosure.
Figure 3:
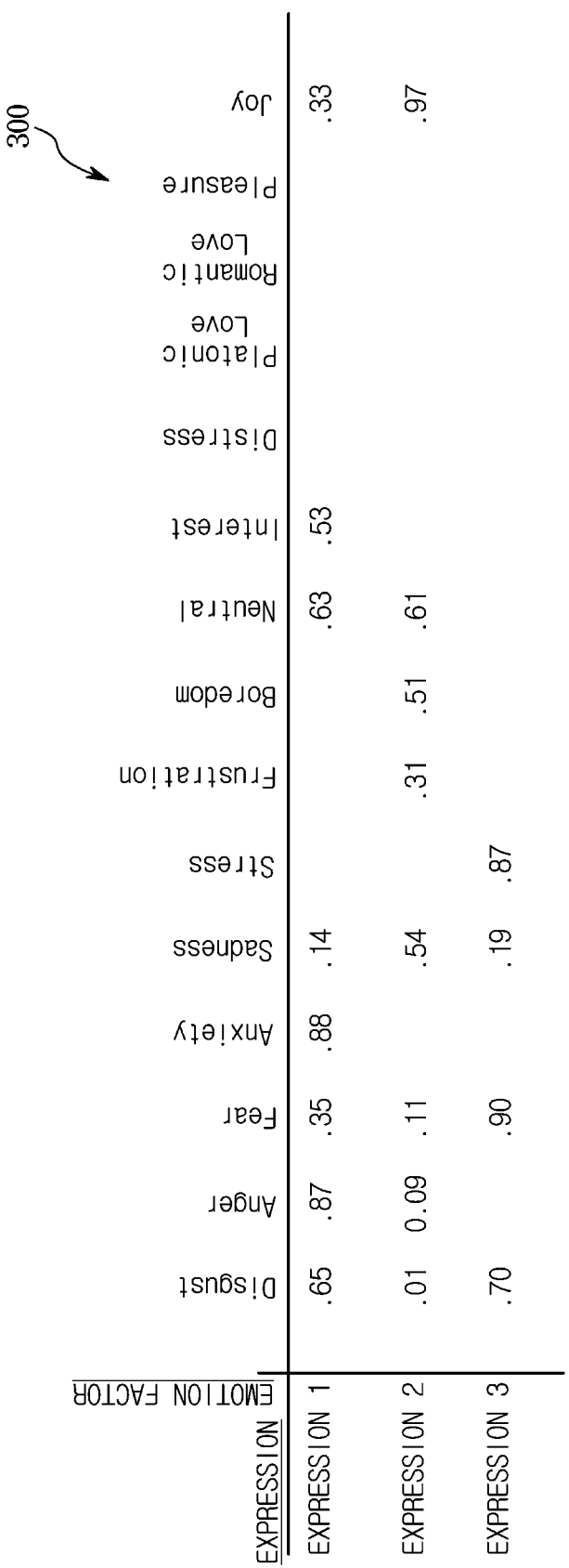
FIG. 3 is a view illustrating correlation information between facial expressions and emotion factors according to embodiments of the present disclosure.
Figure 4:
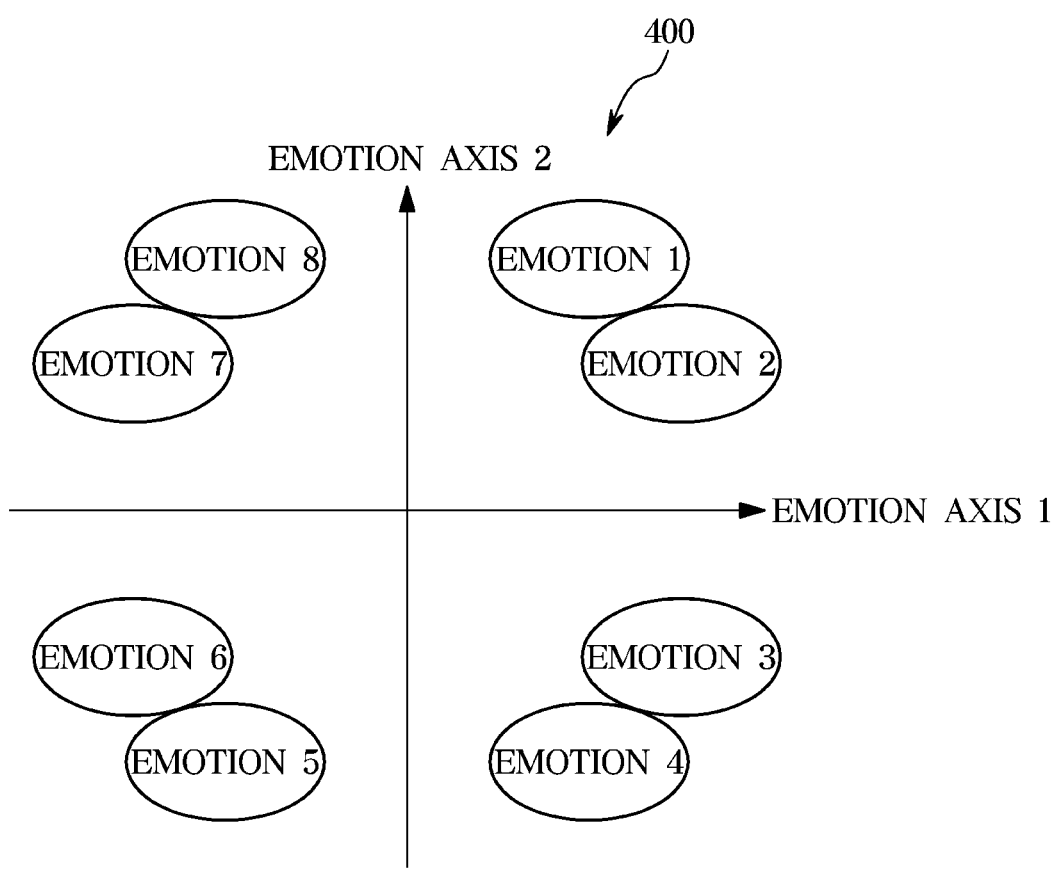
FIG. 4 is a view illustrating an emotion model according to embodiments of the present disclosure.

FIG. 2 is a view illustrating correlation information between bio-signals and emotion factors according to embodiments of the present disclosure, FIG. 3 is a view illustrating correlation information between facial expressions and emotion factors according to embodiments of the present disclosure, and FIG. 4 is a view illustrating an emotion model according to embodiments of the present disclosure.

Referring first to FIG. 2, correlation information 200 between the bio-signal and the emotion factor may include correlation information between the GSR and the EEG and emotion factors.

As illustrated in FIG. 2, a GSR signal has correlation values of 0.875 and 0.775 with emotion factors of Disgust and Anger, respectively, which indicates that the GSR signal has a high relevance with the emotion factors of Disgust and Anger. Therefore, a bio-signal of the user collected by a GSR sensor may be the basis on which an emotion of the user is determined as an anger emotion or a disgust emotion.

An emotion factor of Joy has a relatively low correlation value of 0.353 with a GSR signal, which indicates that the emotion factor of Joy is less relevant to the GSR signal.

An EEG signal has correlation values of 0.864 and 0.878 with emotion factors of Anger and Fear, respectively, which indicates that the EEG signal has a relatively higher relevance to the emotion factors of Anger and Fear than the other emotion factors. Therefore, a bio-signal collected by a EEG sensor may be the basis on which an emotion of the user is determined as an anger emotion or a fear emotion.

In this way, the controller 140 may obtain emotion information of each of the users by using the correlation information 200 between bio-signals and emotion factors. However, because the information illustrated in FIG. 2 is of experimental results, it may vary depending on experimental environments.

Although correlation information between the GSR and the EEG and emotion factors is illustrated in FIG. 2, the correlation information 200 between the bio-signals and the emotion factors may include correlation information between different bio-signals and emotion factors depending on the kinds of bio-signals measured by sensors provided in the vehicle 10.

Referring next to FIG. 3, the controller 140 according to embodiments of the present disclosure may recognize a facial expression of each of the users appearing on an image of the user captured by the camera 110, and obtain emotion information of the user by applying a facial action coding system (FACS) to the facial expression of the user.

More particularly, the controller 140 may extract a plurality of feature points from a face of the user, and extract a plurality of facial elements by using the extracted feature points. The plurality of facial elements may include eyebrows, eyes, nose, mouth, and the like. The controller 140 may combine patterns of the plurality of facial elements, and compare the combined pattern with correlation information 300 between facial expressions and emotion factors stored in the storage 160. The correlation information 300 between facial expressions and emotion factors may correspond to information representing relationships between facial expressions and emotion factors.

The controller 140 may determine a facial expression corresponding to the same pattern as or the most similar pattern to the combined pattern of the user in the correlation information 300 between facial expressions and emotion factors, and determine the searched facial expression as a facial expression of the user.

In addition, the controller 140 may obtain emotion information representing an emotion of the user by considering a correlation value for the determined facial expression of the user in the correlation information 300 between facial expressions and emotion factors.

For example, when the determined facial expression of the user corresponds to a facial expression 2 in the correlation information 300 between facial expressions and emotion factors, the controller 140 may obtain emotion information representing that an emotion of the user is a joy emotion having a highest correlation value for the facial expression 2.

In FIG. 3, the correlation information 300 between facial expressions and emotion factors includes a facial expression 1, the facial expression 2, and a facial expression 3, however, the correlation information 300 may further include another facial expression that may represent a passenger's emotion.

In this way, the controller 140 may analyze an image of the inside of the vehicle 10, photographed by the camera 110, to determine a facial expression of each of the users in the vehicle 10 and to obtain emotion information of the user based on the determined facial expression.

Referring next to FIG. 4, an emotion model 400 may be a graph illustrating emotions of the user classified according to image data of the user and bio-signals of the user.

The emotion model 400 may classify the emotions of the user on the basis of predetermined emotion axes. The emotion axes may be determined based on emotions measured from images of the user or from bio-signals of the user. For example, emotional axis 1 may be degrees of positivity or negativity, which are measurable by voices or facial expressions of the user, and emotional axis 2 may be degrees of excitability or activity, which are measurable by the GSR or the EEG.

When an emotion of the user has a high degree of positivity and a high degree of excitability, the emotion may be classified to emotion 1 or emotion 2. Conversely, when an emotion of the user has minus (−) positivity, i.e., a high degree of negativity and a high degree of excitability, the emotion may be classified to emotion 3 or emotion 4.

The emotion model may be a Russell's emotion model. The Russell's emotional model may be expressed by a two-dimensional graph based on the x-axis and the y-axis, and may classify emotions to eight areas of joy (0 degrees), excitement (45 degrees), arousal (90 degrees), pain (135 degrees), unpleasantness (180 degrees), depression (225 degrees), sleepiness (270 degrees), and relaxation (315 degrees). In addition, the eight areas may comprise a total of 28 emotions that are classified into similar emotions belonging to the eight areas.

In this way, the controller 140 may obtain emotion information of each of the users by using facial expressions and bio-signals of the user, the correlation information 200 between bio-signals and emotion factors, the correlation information 300 between facial expressions and emotion factors, and the emotion model 400.

At this time, the obtained emotion information may be defined as numerical values for the degree of positivity and degree of excitability according to the degrees of emotions. Particularly, each degree of positivity and degree of excitability may be expressed numerically as a value between −100 and 100 depending on the degrees. However, the numerical values according to the degrees are merely an example, and may be included without limitation as long as it corresponds to numerical values that can represent the degrees.

Hereinafter, the manner in which the vehicle 10 according to embodiments of the present disclosure controls the feedback device 150 will be described in detail.

Figure 5:
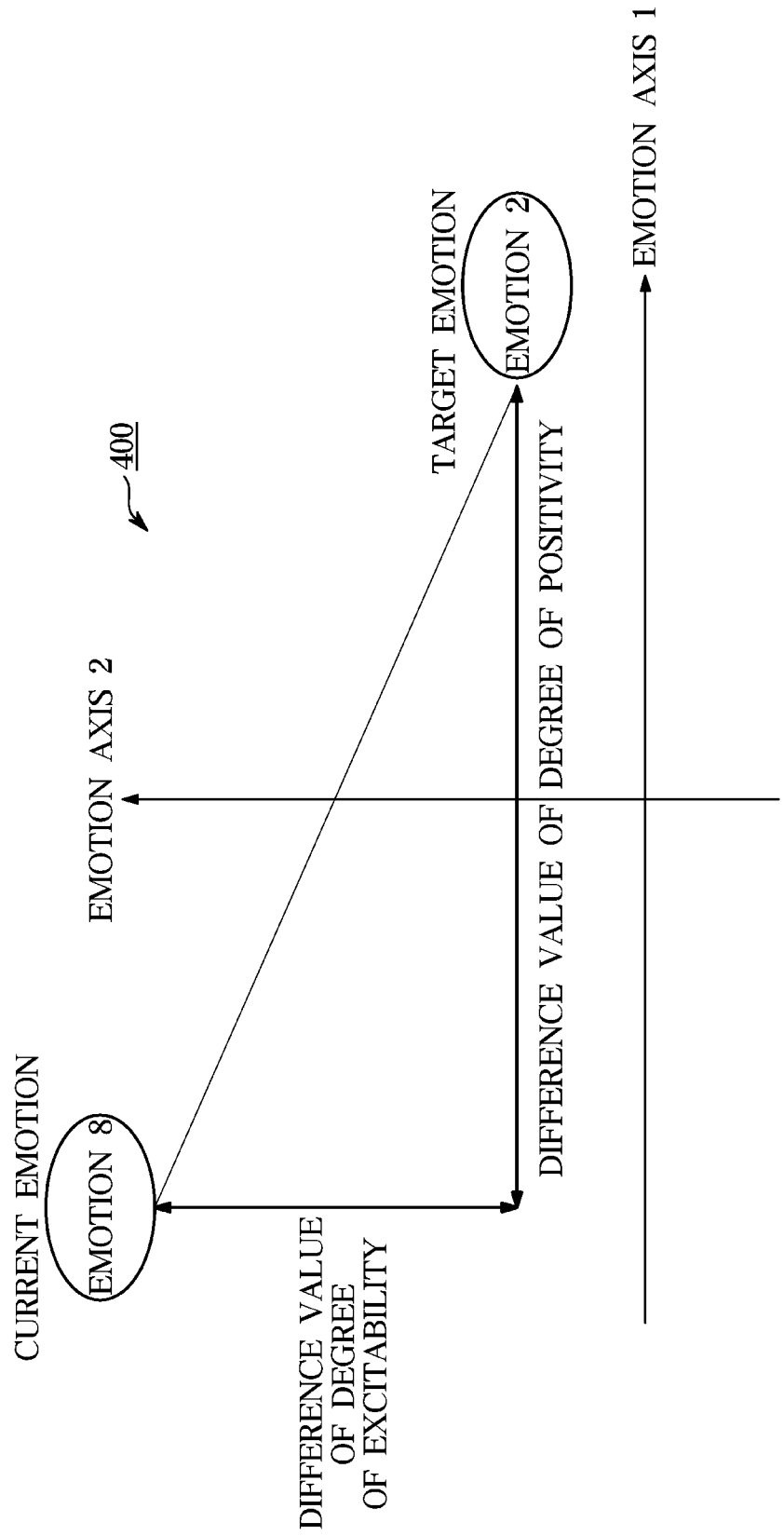
FIG. 5 is a view illustrating a difference value between a current emotional state and a target emotional state according to embodiments of the present disclosure.
Figure 6:
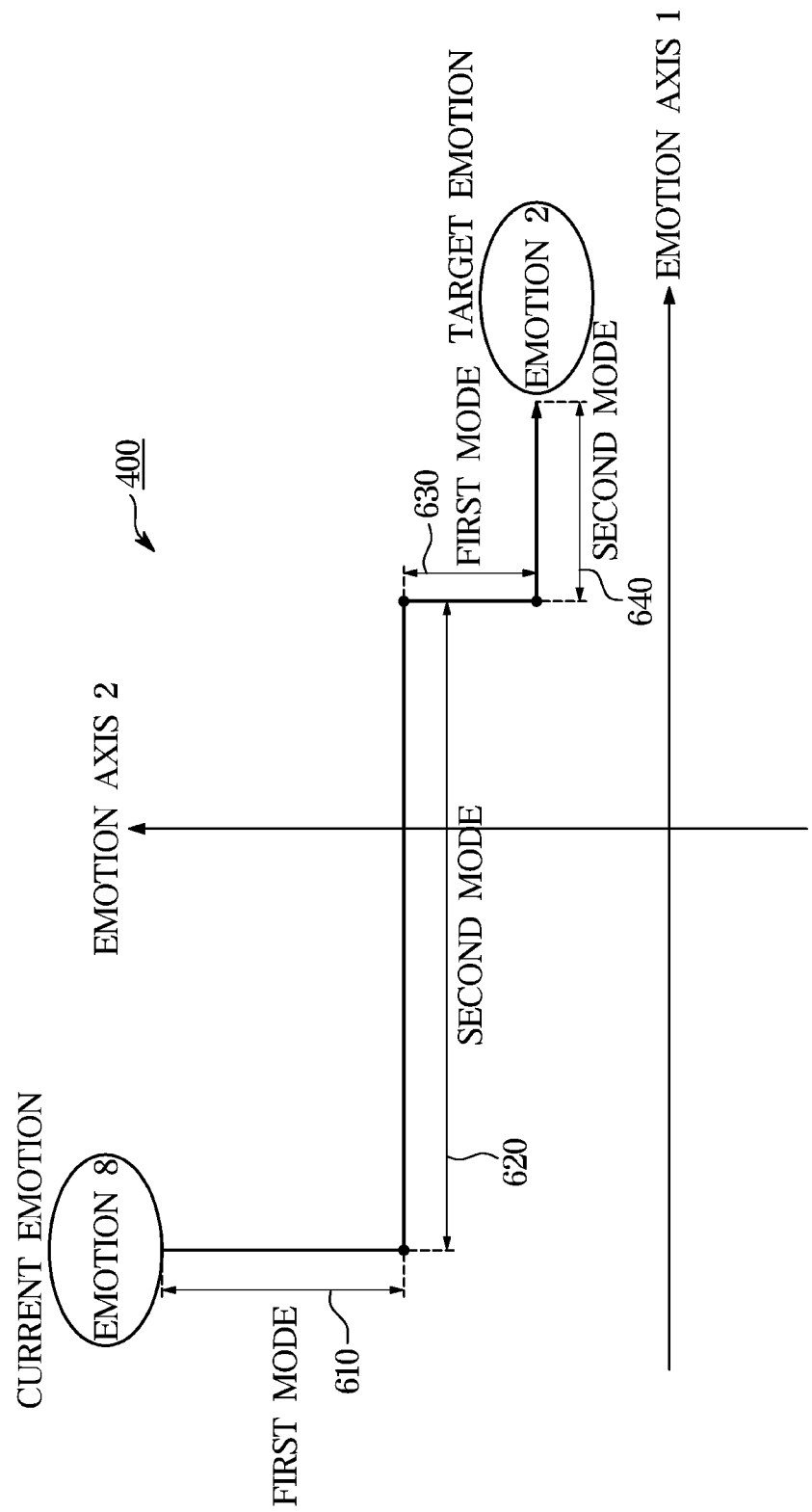
FIG. 6 is a view illustrating mode switching of a feedback device according to embodiments of the present disclosure.

FIG. 5 is a view illustrating a difference value between a current emotional state and a target emotional state according to embodiments of the present disclosure, FIG. 6 is a view illustrating mode switching of a feedback device according to embodiments of the present disclosure, and FIG. 7 is a view illustrating control of the feedback device according to each mode in the vehicle according to embodiments of the present disclosure.

Referring first to FIG. 5, the controller 140 may determine the user's current emotional state based on at least one of image data of the user and bio-signals.

For example, the determined user's current emotional state may be classified as emotion 8, which has a high degree of excitability and a high degree of negativity. That is, the information characterizing the current emotional state may indicate plus (+) excitability and minus (−) positivity, and each degree of positivity and degree of excitability may be expressed numerically according to the degrees.

The controller 140 may control the feedback device 150 based on the determined current emotional state.

Particularly, the controller 140 may compare the degree of excitability of the user and the degree of positivity of the user indicated by the current emotional state, and select either the first mode for controlling the feedback device 150 in a direction of decreasing the degree of excitability of the user or the second mode for controlling the feedback device 150 in a direction of increasing the degree of positivity of the user based on the comparison result. That is, the controller 140 may determine the operation ratio between the first mode and the second mode to 100 to 0 or 0 to 100 for immediate feedback on the current emotional state according to the embodiment. Accordingly, the controller 140 may control the feedback device 150 to operate in either the first mode or the second mode.

In this case, when the numerical value of the degree of excitability indicated by the current emotional state is higher than the numerical value of the degree of negativity indicated by the current emotional state, the controller 140 may control the feedback device 150 to operate in the first mode. When the numerical value of the degree of excitability indicated by the current emotional state is lower than the numerical value of the degree of negativity indicated by the current emotional state, the controller 140 may control the feedback device 150 to operate in the second mode.

At this time, the numerical value of the degree of negativity may correspond to a numerical value of the degree of positivity having a minus (−) value, and may correspond to a case where the emotional state is located on a second quadrant and a third quadrant on the emotion model 400. In the comparison between the numerical value of the degree of excitability and the numerical value of the degree of negativity, it is premised that the comparison is made based on the absolute value of each numerical value.

In addition, the controller 140 may determine the operation ratio between the first mode and the second mode based on the difference value between the user's current emotional state and the target emotional state, and control the feedback device 150 based on the determined operation ratio for the predetermined time.

The controller 140 may determine the difference value between the user's current emotional state and the target emotional state based on at least one of the image data of the user and the bio-signal. The target emotional state may be set when the vehicle 10 is designed, or may be set based on the user's input through the inputter 130. For example, the target emotional state may correspond to emotion 2, which has a low degree of excitability and a high degree of positivity.

As illustrated in FIG. 5, the difference value between the user's current emotional state and the target emotional state may include a difference value for the degree of excitability and a difference value for the degree of positivity. That is, the controller 140 may compare the degree of excitability and the degree of positivity of the target emotional state on the basis of the determined degree of excitability and the determined degree of positivity, respectively, and determine the difference value for the degree of excitability and the difference value for the degree of positivity.

At this time, the controller 140 may determine the operation ratio between the first mode and the second mode so as to correspond to the ratio between the difference value for the degree of excitability and the difference value for the degree of positivity between the current emotional state and the target emotional state.

Thereafter, the controller 140 may control the feedback device 150 to perform the first mode for a first time of the predetermined time based on the determined operation ratio. The controller 140 may control the feedback device 150 to perform the second mode for a second time of the predetermined time, the second time equaling a difference between the predetermined time and the first time.

That is, the ratio between the first time and the second time may correspond to the operation ratio determined by the controller 140.

For example, referring next to FIG. 6, the sum of the times of a first section 610 and a third section 630 in which the feedback device 150 operates in the first mode may be the first time. The sum of the times of a second section 620 and a fourth section 640 in which the feedback device 150 operates in the second mode may be the second time which equals a difference between the predetermined time and the first time.

The predetermined time may be set when the vehicle 10 is designed, or may be set based on the user's input through the inputter 130. In addition, the predetermined time may correspond to the estimated driving time to a destination calculated by the controller 140 according to the user's destination input through the inputter 130.

The controller 140 may control the feedback device 150 such that the first mode and the second mode are repeatedly alternately performed based on the predetermined number of mode switching times and the predetermined holding time for each mode.

The predetermined number of mode switching times and the predetermined holding time for each mode may be set when the vehicle 10 is designed, or may be set based on the user's input through the inputter 130.

For example, referring next to FIG. 6, the predetermined number of mode switching times may correspond to '3,' and the holding time for each mode may be set differently for each of the intervals 610, 620, 630, and 640. However, the ratio of the total operation time for each mode may correspond to the operation ratio determined by the controller 140. However, the operation pattern of the feedback device 150 illustrated in FIG. 6 is merely an example, and various operation patterns may be prepared according to the setting.

That is, the controller 140 may control the feedback device 150 such that the first mode and the second mode are repeatedly alternately performed. At this time, the total time that the feedback device 150 operates in the first mode may correspond to the first time of the predetermined time, and the total time that the feedback device 150 operates in the second mode may correspond to a second time of the predetermined time, the second time equaling a difference between the predetermined time and the first time.

In addition, the controller 140 may perform an operation through a neural network on the current emotional state and the target emotional state, determine the number of mode switching times and the holding time for each mode corresponding to the current emotional state and the target emotional state based on information characterizing the operation performed through the neural network, and control the feedback device 150 such that the first mode and the second mode are repeatedly alternately performed based on the determined number of mode switching times and the determined holding time for each mode.

Particularly, the controller 140 may perform the operation through the neural network on the determined current emotional state and the target emotional state, determine the number of mode switching times, and determine an operation pattern of the feedback device 150 based on the information characterizing the operation performed through the neural network.

At this time, the operation pattern of the feedback device 150 may correspond to the mode in which the feedback device 150 operates by switching the mode for the predetermined time based on the number of times an operation mode is switched for the predetermined time and the holding time for each mode.

In this case, the information characterizing the operation performed through the neural network may include information characterizing the number of mode switching times indicating the number of times the mode is switched during the predetermined time and information characterizing the holding time for each mode indicating the time at which the mode for each mode to be switched is held.

The above-mentioned neural network refers to the machine learning that forms the neural structure capable of performing deep learning, so that the weight and bias corresponding to the configuration of the neural network continuously changes, thereby improving the reliability of learning.

Particularly, the vehicle 10 may improve the inference result of the neural network by continuously updating the weight, bias and activation function included in the neural network based on the current emotional state, the target emotional state, and information characterizing an arrival time of the user's emotion according to the pattern of the feedback device 150 to the target emotion. That is, the vehicle 10 may store the determined pattern and the information characterizing the arrival time of the user's emotion to the target emotion whenever the vehicle 10 drives, and continuously update the stored neural network based on information characterizing the stored determined pattern and the information characterizing the arrival time.

Meanwhile, the neural network may include the CNN that generates the feature map output by convoluting the current emotional state and the target emotional state, and inputs the feature map to the neural network. However, the neural network may be performed with other deep-running algorithms including the RNN.

In this way, the vehicle 10 may determine the operation pattern of the feedback device 150 that is most suitable based on the current emotional state and the target emotional state through the neural network that is continuously updated according to the use. That is, the controller 140 may determine the number of mode switching times and the holding time for each mode in which the user's emotion can quickly reach the target emotion, based on the current emotional state and the target emotional state.

However, the controller 140 may control the feedback device 150 to operate in either the first mode or the second mode based on the user's input through the inputter 130.

Hereinafter, the control of the feedback device 150 of the controller 140 according to the modes will be described in detail.

The controller 140 may extract the emotion factor that affects the user's current emotional state and control the feedback device 150 in the direction of decreasing the emotion factor corresponding to the degree of excitability of the extracted emotion factor in the first mode, and control the feedback device 150 in the direction of increasing the emotion factor corresponding to the degree of positivity of the extracted emotion factors in the second mode.

Referring next to FIG. 7, the feedback device 150 may include at least one of the speaker 151, the display 152, the air conditioner 154 provided in the vehicle 10, and the vibration device 153 provided in the seat of the vehicle 10.

The speaker 151 may output sound to the inside of the vehicle 10 having a frequency corresponding to the target breathing cycle or the target heartbeat cycle in the first mode under the control of the controller 140, or output sound to the inside of the vehicle 10 that increases the emotion factor corresponding to the degree of positivity in the second mode under the control of the controller 140.

That is, the controller 140 may set the breathing cycle and the heartbeat cycle when the target emotional state is the target breathing cycle and the target heartbeat cycle, respectively, and control the speaker 151 to output sound corresponding to the target breathing cycle or the target heartbeat cycle to the inside of the vehicle 10 so that the degree of excitability of the user is decreased in the first mode. Accordingly, the vehicle 10 can cause the user's breathing cycle to be induced to the target breathing cycle or the user's heartbeat cycle to be induced to the target heartbeat cycle.

At this time, the sound that increases the emotion factor corresponding to the degree of positivity may be set when the vehicle 10 is designed, and may correspond to sound that has at least one of the size, the genre, the equalizer, the tone color, and the sound wave region of the sound in which the user can feel the positive emotion. For example, the sound that increases the emotion factor corresponding to the degree of positivity may include hip-hop music, classical music, and pop music in which the user can feel the positive emotion. However, the sound that increases the emotion factor corresponding to the degree of positivity may be set based on the user's input through the inputter 130. That is, the user may set the sound that caused the positive emotion to be the sound that increases the emotion factor corresponding to the degree of positivity, and the sound that is set can be stored in the storage 160.

The display 152 according to embodiments of the present disclosure may output the image having a frequency corresponding to the target breathing cycle or the target heartbeat cycle to the inside of the vehicle 10 in the first mode, and output the image having the frequency corresponding to the sound for increasing the emotion factor corresponding to the degree of positivity to the inside of the vehicle 10 in the second mode, under the control of the controller 140.

More particularly, the controller 140 may control the display 152 to increase or decrease the intensity of light output according to the frequency corresponding to the target breathing cycle or the target heartbeat cycle in the first mode, and control the display 152 to increase or decrease the intensity of the light output according to the frequency corresponding to the sound that increases the emotion factor corresponding to the degree of positivity in the second mode.

The display 152 may also output the image of a color that decreases the emotion factor corresponding to the degree of excitability in the first mode based on the control of the controller 140, and output the image of the color that increases the emotion factor corresponding to the positivity of the image in the second mode, under the control of the controller 140.

At this time, the color for decreasing the emotion factor corresponding to the degree of excitability and the color for increasing the emotion factor corresponding to the degree of positivity may be set when the vehicle 10 is designed, may be set by the controller 140 based on correlation information between the color and the emotion factor obtained from the external server, and may be set by the user through the inputter 130.

The vibration device 153 according to embodiments of the present disclosure may output the vibration having a frequency corresponding to the target breathing cycle or the target heartbeat cycle in the first mode, or output the vibration having the frequency corresponding to the sound for increasing the emotion factor corresponding to the degree of positivity in the second mode, under the control of the controller 140.

At this time, the outputted vibration causes the seat provided in the vehicle 10 to vibrate, and may be transmitted to the user located on the seat through the seat.

The air conditioner 154 may output at least one of the perfume and wind that decreases the emotion factor corresponding to the degree of excitability in the first mode, and output at least one of the perfume and wind that increases the emotion factor corresponding to the degree of positivity in the second mode, under the control of the controller 140.

At this time, the perfume and wind that decrease the emotion factor corresponding to the degree of excitability may be set when the vehicle 10 is designed, may be set by the controller 140 based on the correlation information between the perfume and the emotion factor obtained from the external server, and may be set by the user through the inputter 130. For example, the perfume and wind that decrease the emotion factor corresponding to the degree of excitability may correspond to jasmine perfume and a breeze, respectively. However, the present disclosure is not limited thereto, and any perfume that can decrease the emotion factor corresponding to the degree of excitability may be included without limitation. Also, the wind that decreases the emotion factor corresponding to the degree of excitability may correspond to wind having at least one of wind direction, intensity, and temperature that can lower the degree of excitability.

In addition, the perfume and wind that decrease the emotion factor corresponding to the degree of positivity may be set when the vehicle 10 is designed, may be set by the controller 140 based on the correlation information between the perfume and the emotion factor obtained from the external server, and may be set by the user through the inputter 130. For example, the perfume and wind that increase the emotion factor corresponding to the degree of positivity may correspond to lemon perfume and a cool breeze, respectively. However, the present disclosure is not limited thereto, and any perfume that can increase the emotion factor corresponding to the degree of positivity may be included without limitation. Also, the wind that increases the emotion factor corresponding to the degree of positivity may correspond to wind having at least one of wind direction, intensity, and temperature that can raise the degree of positivity.

In this way, the controller 140 may control at least one of the speaker 151, the display 152, the vibration device 153, and the air conditioner 154 corresponding to the feedback device 150 to induce the user's positive emotion and decrease the degree of excitability of the user.

Hereinafter, a control method of the vehicle 10 according to embodiments of the present disclosure will be described. The vehicle 10 according to the above-described embodiment of the present disclosure may be applied to the control method of the vehicle 10, as will be described below. Therefore, descriptions given above with reference to FIGS. 1 to 7 may be applied to the control method of the vehicle 10 in the same manner, unless otherwise noted.

FIG. 8 is a flowchart illustrating a method of controlling the feedback device in a method of controlling the vehicle according to embodiments of the present disclosure.

As shown in FIG. 8, the vehicle 10 according to embodiments of the present disclosure may determine information characterizing the user's current emotional state based on at least one of the bio-signal or the image information (810).

Particularly, the controller 140 may determine the facial expression of the user based on the image data of the user, and obtain information characterizing the emotional state corresponding to the facial expression. At this time, the image information may be obtained by the camera 110 provided in the vehicle 10.

In addition, the controller 140 may obtain information characterizing the user's emotional state corresponding to the bio-signal of the user based on the bio-signal of the passenger 200. At this time, the bio-signal may be obtained by the bio-signal sensor 120 provided in the vehicle 10.

At this time, the information characterizing the current emotional state may be indicated by the numerical value in which each degree of positivity and degree of excitability is expressed numerically according to the degrees.

The vehicle 10 may compare the degree of excitability of the user and the degree of positivity of the user indicated by the current emotional state (820).

Particularly, the controller 140 may compare the degree of excitability of the user and the degree of positivity of the user indicated by the current emotional state, and select either the first mode for controlling the feedback device 150 in a direction of decreasing the degree of excitability of the user or the second mode for controlling the feedback device 150 in a direction of increasing the degree of positivity of the user based on the comparison result. That is, the controller 140 may determine the operation ratio between the first mode and the second mode to 100 to 0 or 0 to 100 for immediate feedback on the current emotional state according to the embodiment. Accordingly, the controller 140 may control the feedback device 150 to operate in either the first mode or the second mode.

Particularly, the controller 140 may compare the numerical value of the degree of excitability of the user with the numerical value of the degree of negativity of the user, i.e., the minus (−) degree of positivity, based on information characterizing the current emotional state.

At this time, the numerical value of the degree of negativity may correspond to a numerical value of the degree of positivity having a minus (−) value, and may correspond to a case where the emotional state is located on a second quadrant and a third quadrant on the emotion model 400. In the comparison between the numerical value of the degree of excitability and the numerical value of the degree of negativity, it is premised that the comparison is made based on the absolute value of each numerical value.

The vehicle 10 may select either the first mode for controlling the feedback device 150 in a direction of decreasing the degree of excitability of the user or the second mode for controlling the feedback device 150 in a direction of increasing the degree of positivity of the user based on the comparison result (830).

In this case, when the numerical value of the degree of excitability indicated by the current emotional state is higher than the numerical value of the degree of negativity indicated by the current emotional state, the controller 140 may control the feedback device 150 to operate in the first mode. When the numerical value of the degree of excitability indicated by the current emotional state is lower than the numerical value of the degree of negativity indicated by the current emotional state, the controller 140 may control the feedback device 150 to operate in the second mode.

That is, the controller 140 may determine the operation ratio between the first mode and the second mode to 100 to 0 or 0 to 100 for immediate feedback on the current emotional state according to the embodiment. Accordingly, the controller 140 may control the feedback device 150 to operate in either the first mode or the second mode.

In addition, the vehicle 10 may control the feedback device 150 based on the selected mode (840).

That is, the controller 140 may control at least one of the speaker 151, the display 152, the vibration device 153, and the air conditioner 154 corresponding to the feedback device 150 to induce the user's positive emotion and decrease the degree of excitability of the user.

The configuration in which the controller 140 controls the feedback device 150 is the same as that described above, thus a detailed explanation will be omitted.

Hereinafter, a control method of the vehicle 10 for the case where the vehicle 10 may determine the operation ratio between the first mode and the second mode based on the difference value between the user's current emotional state and the target emotional state, and control the feedback device 150 based on the determined operation ratio for the predetermined time will be described.

FIG. 9 is another flowchart illustrating a method of controlling the feedback device in a method of controlling the vehicle according to embodiments of the present disclosure.

As shown in FIG. 9, the vehicle 10 according to embodiments of the present disclosure may determine information characterizing the user's current emotional state based on at least one of the bio-signal or the image information (910).

Particularly, the controller 140 may determine the facial expression of the user based on the image data of the user, and obtain information characterizing the emotional state corresponding to the facial expression. At this time, the image information may be obtained by the camera 110 provided in the vehicle 10.

In addition, the controller 140 may obtain information characterizing the user's emotional state corresponding to the bio-signal of the user based on the bio-signal of the passenger 200. At this time, the bio-signal may be obtained by the bio-signal sensor 120 provided in the vehicle 10.

At this time, the information characterizing the current emotional state may be indicated by the numerical value in which each of the degree of positivity and degree of excitability is expressed numerically according to the degrees.

The vehicle 10 may determine the difference value for the degree of excitability and the difference value for the degree of positivity between the current emotional state and the target emotional state (920).

That is, the vehicle 10 may determine the difference value between the user's current emotional state and the target emotional state based on at least one of the image data of the user and the bio-signal. The target emotional state may be set when the vehicle 10 is designed, or may be set based on the user's input through the inputter 130. For example, the target emotional state may correspond to emotion 2, which has the low degree of excitability and the high degree of positivity.

The difference value between the user's current emotional state and the target emotional state may include the difference value for the degree of excitability and the difference value for the degree of positivity. That is, the controller 140 may compare the degree of excitability and the degree of positivity of the target emotional state on the basis of the determined degree of excitability and the determined degree of positivity, respectively, and determine the difference value for the degree of excitability and the difference value for the degree of positivity.

The vehicle 10 may determine the operation ratio between the first mode and the second mode so as to correspond to the ratio between the difference value for the degree of excitability and the difference value for the degree of positivity (930).

In addition, the vehicle 10 may control the feedback device 150 for the predetermined time based on the determined operation ratio (940).

Particularly, the controller 140 may control the feedback device 150 to perform the first mode for the first time of the predetermined time based on the determined operation ratio. The controller 140 may control the feedback device 150 to perform the second mode for the second time which equals a difference between the predetermined time and the first time.

That is, the ratio between the first time and the time excluding the first time of the predetermined time may correspond to the operation ratio determined by the controller 140.

The predetermined time may be set when the vehicle 10 is designed, or may be set based on the user's input through the inputter 130. In addition, the predetermined time may correspond to the estimated driving time to a destination calculated by the controller 140 according to the user's destination input through the inputter 130.

The controller 140 may control the feedback device 150 such that the first mode and the second mode are repeatedly alternately performed based on the predetermined number of mode switching times and the predetermined holding time for each mode.

The predetermined number of mode switching times and the predetermined holding time for each mode may be set when the vehicle 10 is designed, or may be set based on the user's input through the inputter 130.

That is, the controller 140 may control the feedback device 150 such that the first mode and the second mode are repeatedly alternately performed. At this time, the total time that the feedback device 150 operates in the first mode may correspond to the first time of the predetermined time, and the total time that the feedback device 150 operates in the second mode may correspond to a second time of the predetermined time, the second time equaling a difference between the predetermined time and the first time.

In addition, the controller 140 may perform an operation through a neural network on the current emotional state and the target emotional state, determine the number of mode switching times and the holding time for each mode corresponding to the current emotional state and the target emotional state based on information characterizing the operation performed through the neural network, and control the feedback device 150 such that the first mode and the second mode are repeatedly alternately performed based on the determined number of mode switching times and the determined holding time for each mode.

Particularly, the controller 140 may perform the operation through the neural network on the determined current emotional state and the target emotional state, determine the number of mode switching times, and determine the operation pattern of the feedback device 150 based on the information characterizing the operation performed through the neural network.

At this time, the operation pattern of the feedback device 150 may correspond to the mode in which the feedback device 150 operates by switching the mode for the predetermined time based on the number of times an operation mode is switched for the predetermined time and the holding time for each mode.

In this case, the information characterizing the operation performed through the neural network may include information characterizing the number of mode switching times indicating the number of times the mode is switched during the predetermined time and information characterizing the holding time for each mode indicating the time at which the mode for each mode to be switched is held.

The above-mentioned neural network refers to the machine learning that forms the neural structure capable of performing deep learning, so that the weight and bias corresponding to the configuration of the neural network continuously changes, thereby improving the reliability of learning.

Particularly, the vehicle 10 may improve the inference result of the neural network by continuously updating the weight, bias and activation function included in the neural network based on the current emotional state, the target emotional state, and information characterizing an arrival time of the user's emotion according to the pattern of the feedback device 150 to the target emotion. That is, the vehicle 10 may store the determined pattern and the information characterizing the arrival time of the user's emotion to the target emotion whenever the vehicle 10 drives, and continuously update the stored neural network based on information characterizing the stored determined pattern and the information characterizing the arrival time.

In this way, the vehicle 10 may determine the operation pattern of the feedback device 150 that is most suitable based on the current emotional state and the target emotional state through the neural network that is continuously updated according to the use. That is, the controller 140 may determine the number of mode switching times and the holding time for each mode in which the user's emotion can quickly reach the target emotion, based on the current emotional state and the target emotional state.

The configuration in which the controller 140 controls the feedback device 150 is the same as that described above, thus a detailed explanation will be omitted.

According to the vehicle and the method for controlling the vehicle as described above, by determining a mode in which the user's emotional state in the vehicle is determined as a degree of positivity and a degree of excitability, and determining an operation ratio between a mode for controlling a feedback device so as to decrease the degree of excitability and a mode for controlling the feedback device so as to increase the degree of positivity according to the determined degree of positivity and degree of excitability, the user's emotion can be promptly caused to the target emotion.

The exemplary embodiments of the present disclosure have thus far been described with reference to the accompanying drawings. It will be obvious to those of ordinary skill in the art that the present disclosure may be practiced in other forms than the exemplary embodiments as described above without changing the technical idea or essential features of the present disclosure. The above exemplary embodiments are only by way of example, and should not be interpreted in a limited sense.

What is claimed is:

1. A vehicle comprising:
   a feedback device;
   a bio-signal sensor configured to measure a bio-signal of a user; and
   a controller operatively coupled to the feedback device and the bio-signal sensor, the controller including a memory configured to store at least one program instruction and processor configured to execute the at least one program instruction, and the controller being configured to:
   determine information characterizing a current emotional state of the user based on the bio-signal;
   calculate, based on a difference value between the current emotional state and a target emotional state, an operation ratio between a first mode for controlling operation of the feedback device to decrease a degree of excitability of the user and a second mode for controlling the operation of the feedback device to increase a degree of positivity of the user;
   control the operation of the feedback device for a predetermined time based on the operation ratio;
   calculate a first difference value between the degree of excitability for the current emotional state and the degree of excitability for the target emotional state calculate;
   calculate a second difference value between the degree of positivity for the current emotional state and the degree of positivity for the target emotional state calculate; and calculate the operation ration between the first mode and the second mode as equivalent to a ratio between the first difference value and the second difference value.

2. The vehicle according to claim 1, wherein the controller is configured to control the operation of the feedback device, based on the operation ratio, such that the feedback device performs the first mode for a first time of the predetermined time and performs the second mode for a second time of the predetermined time, wherein the second time equals a difference between the predetermined time and the first time.

3. The vehicle according to claim 2, wherein the controller is configured to control the operation of the feedback device such that the first mode and the second mode are repeatedly alternately performed based on a predetermined number of mode switching times and a predetermined holding time for each mode.

4. The vehicle according to claim 1, wherein the controller is configured to determine the degree of excitability of the user and the degree of positivity of the user based on the current emotional state, to compare the degree of excitability of the user with the degree of positivity of the user, and to perform either the first mode or the second mode based on the comparison of the degree of excitability of the user with the degree of positivity of the user.

5. The vehicle according to claim 1, wherein the feedback device is disposed in the vehicle and comprises at least one of a speaker, a display, an air conditioner, and a vibration device installed in a seat.

6. The vehicle according to claim 1, wherein the controller is configured to:
extract an emotion factor that affects the current emotional state;
in the first mode, control the operation of the feedback device causing an emotion factor to decrease according to the degree of excitability of the extracted emotion factor; and
in the second mode, control the operation of the feedback device causing an emotion factor to increase according to the degree of positivity of the extracted emotion factor.

7. A vehicle comprising:
a feedback device;
a bio-signal sensor configured to measure a bio-signal of a user; and
a controller operatively coupled to the feedback device and the bio-signal sensor, the controller including a memory configured to store at least one program instruction and processor configured to execute the at least one program instruction, and the controller being configured to:
determine information characterizing a current emotional state of the user based on the bio-signal;
calculate, based on a difference value between the current emotional state and a target emotional state, an operation ratio between a first mode for controlling operation of the feedback device to decrease a degree of excitability of the user and a second mode for controlling the operation of the feedback device to increase a degree of positivity of the user;
control the operation of the feedback device for a predetermined time based on the operation ratio;
control the operation of the feedback device, based on the operation ratio, such that the feedback device performs the first mode for a first time of the predetermined time and performs the second mode for a second time of the predetermined time, wherein the second time equals a difference between the predetermined time and the first time;
perform an operation through a neural network based on the current emotional state and the target emotional state;
determine the number of mode switching times and the holding time for each mode corresponding to the current emotional state and the target emotional state based on information characterizing the operation performed through the neural network; and
control the operation of the feedback device such that the first mode and the second mode are repeatedly alternately performed based on the determined number of mode switching times and the determined holding time for each mode.

8. A method for controlling a vehicle, the vehicle including a feedback device, a bio-signal sensor configured to measure a bio-signal of a user, and a controller operatively coupled to the feedback device and the bio-signal sensor, the method comprising:
determining, by the controller, information characterizing a current emotional state of the user based on the bio-signal;
calculating, by the controller, based on a difference value between the current emotional state and a target emotional state, an operation ratio between a first mode for controlling the operation of the feedback device to decrease a degree of excitability of the user and a second mode for controlling the operation of the feedback device to increase a degree of positivity of the user; and
controlling, by the controller, the operation of the feedback device for a predetermined time based on the operation ratio;
wherein the calculating of the operation ratio comprises:
calculating a first difference value between the degree of excitability for the current emotional state and the degree of excitability for the target emotional state calculate;
calculating a second difference value between the degree of positivity for the current emotional state and the degree of positivity for the target emotional state calculate; and
calculating the operation ratio between the first mode and the second mode as equivalent to a ratio between the first difference value and the second difference value.

9. The method according to claim 8, wherein the feedback device is disposed in the vehicle and comprises at least one of a speaker, a display, an air conditioner, and a vibration device installed in a seat.

10. The method according to claim 8, wherein the controlling of the operation of the feedback device comprises:
extracting an emotion factor that affects the current emotional state;
in the first mode, controlling the operation of the feedback device causing an emotion factor to decrease according to the degree of excitability of the extracted emotion factor; and
in the second mode, controlling the operation the feedback device causing an emotion factor to increase according to the degree of positivity of the extracted emotion factor.

11. A method for controlling a vehicle, the vehicle including a feedback device, a bio-signal sensor configured to measure a bio-signal of a user, and a controller operatively coupled to the feedback device and the bio-signal sensor, the method comprising:

determining, by the controller, information characterizing a current emotional state of the user based on the bio-signal;

calculating, by the controller, based on a difference value between the current emotional state and a target emotional state, an operation ratio between a first mode for controlling the operation of the feedback device to decrease a degree of excitability of the user and a second mode for controlling the operation of the feedback device to increase a degree of positivity of the user; and controlling, by the controller, the operation of the feedback device for a predetermined time based on the operation ratio;

wherein the controlling of the feedback device comprises controlling the operation of the feedback device, based on the operation ratio, such that the feedback device performs the first mode for a first time of the predetermined time and performs the second mode for a second time of the predetermined time, wherein the second time equals a difference between the predetermined time and the first time.

12. The method according to claim 11, wherein the controlling of the operation of the feedback device comprises:

controlling the operation of the feedback device such that the first mode and the second mode are repeatedly alternately performed based on a predetermined number of mode switching times and a predetermined holding time for each mode.

13. The method according to claim 11, wherein the controlling of the operation of the feedback device comprises:

performing an operation through a neural network based on the current emotional state and the target emotional state;

determining the number of mode switching times and the holding time for each mode corresponding to the current emotional state and the target emotional state based on information characterizing the operation performed through the neural network; and controlling the operation of the feedback device such that the first mode and the second mode are repeatedly alternately performed based on the determined number of mode switching times and the determined holding time for each mode.

14. A method for controlling a vehicle, the vehicle including a feedback device, a bio-signal sensor configured to measure a bio-signal of a user, and a controller operatively coupled to the feedback device and the bio-signal sensor, the method comprising:

determining, by the controller, information characterizing a current emotional state of the user based on the bio-signal;

calculating, by the controller, based on a difference value between the current emotional state and a target emotional state, an operation ratio between a first mode for controlling the operation of the feedback device to decrease a degree of excitability of the user and a second mode for controlling the operation of the feedback device to increase a degree of positivity of the user; and controlling, by the controller, the operation of the feedback device for a predetermined time based on the operation ratio;

wherein the controlling of the operation of the feedback device comprises:

determining the degree of excitability of the user and the degree of positivity of the user based on the current emotional state;

comparing the degree of excitability of the user with the degree of positivity of the user; and performing either the first mode or the second mode based on the comparison of the degree of excitability of the user with the degree of positivity of the user.

* * * * *